US011168629B2

(12) United States Patent
Mizutani et al.

(10) Patent No.: US 11,168,629 B2
(45) Date of Patent: Nov. 9, 2021

(54) EXHAUST GAS ANALYSIS APPARATUS, EXHAUST GAS ANALYSIS METHOD, AND CORRECTION EXPRESSION CREATION METHOD

(71) Applicant: HORIBA, LTD., Kyoto (JP)

(72) Inventors: Naoto Mizutani, Kyoto (JP); Masahiro Nishikawa, Kyoto (JP); Haruhisa Mohara, Kyoto (JP); Shun Fukami, Kyoto (JP); Yosuke Kondo, Kyoto (JP)

(73) Assignee: HORIBA, LTD., Kyoto (JP)

( * ) Notice: Subject to any disclaimer, the term of this patent is extended or adjusted under 35 U.S.C. 154(b) by 214 days.

(21) Appl. No.: 16/564,603

(22) Filed: Sep. 9, 2019

(65) Prior Publication Data
US 2020/0191080 A1 Jun. 18, 2020

(30) Foreign Application Priority Data

Dec. 12, 2018 (JP) .............................. JP2018-232502

(51) Int. Cl.
*F02D 41/02* (2006.01)
*G01N 1/22* (2006.01)
(Continued)

(52) U.S. Cl.
CPC ........... *F02D 41/0235* (2013.01); *G01N 1/22* (2013.01); *G01N 33/0006* (2013.01); *G01N 33/0013* (2013.01); *G01N 27/626* (2013.01)

(58) Field of Classification Search
CPC ........ F23N 5/12–126; F23N 5/08–085; G01N 1/22; G01N 21/76; G01N 21/763; G01N 21/766; G01N 21/00; G01N 2203/0641
(Continued)

(56) References Cited

U.S. PATENT DOCUMENTS 3,384,457 A * 5/1968 Norell .................. G01N 27/626
422/54
3,474,659 A * 10/1969 Kelleher ................ G01N 30/06
73/23.27
(Continued)

FOREIGN PATENT DOCUMENTS

EP 1914545 4/2008
EP 3480593 5/2019
(Continued)

OTHER PUBLICATIONS

L. Leo Ongkiehong, "The Hydrogen Flame Ionization Detector", DOI: 10.6100/IR70383, Jan. 1, 1960, retrieved from the Internet at URL: https://pure.tue.nl/ws/portalfiles/portal/2006369/70383.pdf, 52 pgs.
(Continued)

*Primary Examiner* — Mark A Laurenzi
*Assistant Examiner* — Mickey H France
(74) *Attorney, Agent, or Firm* — Brooks Kushman P.C.

(57) ABSTRACT

The present invention is one that accurately measures an exhaust gas component regardless of variation in atmospheric pressure around a test object that is a vehicle or part of it, and an exhaust gas analysis apparatus that measures component concentration in exhaust gas discharged from the test object that is the vehicle or part of it. The exhaust gas analysis apparatus includes: an exhaust gas detector that mixes the exhaust gas and reactive gas together and detects the resulting phenomenon; a pressure gauge that measures the atmospheric pressure at the time of measurement of the exhaust gas or pressure at a predetermined point inside the exhaust gas analysis apparatus as measured pressure; and a correction part that, on the basis of the measured pressure by the pressure gauge, corrects the measurement error of the
(Continued)

exhaust gas detector associated with a variation in the supply amount of the reactive gas.

12 Claims, 5 Drawing Sheets

(51) Int. Cl.
*G01N 33/00* (2006.01)
*G01N 27/626* (2021.01)

(58) Field of Classification Search
USPC .............. 73/23.31–23.33; 422/52, 54, 82.05; 423/212
See application file for complete search history.

(56) References Cited

U.S. PATENT DOCUMENTS

| | | | |
|---|---|---|---|
| 3,558,283 A * | 1/1971 | Freeman et al. ... | G01N 33/0024 436/143 |
| 3,730,157 A * | 5/1973 | Gerhold .................... | F02D 9/00 123/437 |
| 3,908,365 A * | 9/1975 | Schweibold .............. | F01N 3/28 60/274 |
| 3,973,848 A * | 8/1976 | Jowett .................... | G01M 15/10 356/51 |
| 4,160,373 A * | 7/1979 | Fastaia ................ | G01N 21/3504 340/608 |
| 4,379,402 A | 4/1983 | Harman | |
| 5,547,497 A * | 8/1996 | Klemp .................... | G01N 30/12 73/23.41 |
| 5,633,170 A * | 5/1997 | Neti ..................... | G01N 21/766 423/239.1 |
| 5,922,287 A * | 7/1999 | Kato ..................... | F01N 11/002 422/95 |
| 5,948,966 A * | 9/1999 | Takahashi ............... | F01N 11/00 73/23.31 |
| 6,840,669 B2 * | 1/2005 | Kleinerman ........... | G01K 11/20 250/483.1 |
| 6,962,090 B2 * | 11/2005 | McDonald ........... | G01N 1/2258 73/23.31 |
| 8,280,645 B2 * | 10/2012 | Nakamura ........... | G01N 1/2205 702/24 |
| 2003/0069703 A1 | 4/2003 | Rendahl et al. | |
| 2006/0105279 A1 * | 5/2006 | Munsterhuis ........... | F23N 5/123 431/18 |
| 2007/0077167 A1 * | 4/2007 | Mori .................. | G01N 21/3504 422/54 |
| 2009/0306527 A1 * | 12/2009 | Kubo ..................... | A61B 5/097 600/532 |
| 2010/0005782 A1 * | 1/2010 | Foster ..................... | F01N 3/00 60/277 |
| 2011/0120096 A1 * | 5/2011 | Nakamura .............. | F01N 11/00 60/276 |
| 2011/0131952 A1 * | 6/2011 | Onodera ............ | B01D 53/9445 60/274 |
| 2011/0146378 A1 * | 6/2011 | Brand .................... | G01N 21/64 73/23.31 |
| 2014/0170735 A1 * | 6/2014 | Holmes .................. | G01N 21/07 435/287.1 |
| 2016/0069919 A1 * | 3/2016 | Holmes .............. | G01N 35/0092 506/2 |
| 2016/0115850 A1 * | 4/2016 | Otsuki ................ | G01M 15/102 417/472 |
| 2017/0168033 A1 * | 6/2017 | Yoshimura ......... | G01N 33/0006 |
| 2017/0299505 A1 | 10/2017 | Nishimura | |
| 2017/0343462 A1 * | 11/2017 | Tokuhira ............. | G01M 15/102 |
| 2018/0202845 A1 * | 7/2018 | Kondo .................. | F01N 13/008 |
| 2019/0193056 A1 * | 6/2019 | Hayashi ............... | B01J 35/1014 |
| 2020/0191080 A1 * | 6/2020 | Mizutano ................ | G01N 1/22 |

FOREIGN PATENT DOCUMENTS

| | | |
|---|---|---|
| JP | 2006-284508 | 10/2006 |
| JP | 2018-096962 A | 6/2018 |

OTHER PUBLICATIONS

EESR dated Mar. 20, 2020 issued for European Patent Application No. 19194495.8, 12 pgs.

* cited by examiner

EXHAUST GAS ANALYSIS APPARATUS, EXHAUST GAS ANALYSIS METHOD, AND CORRECTION EXPRESSION CREATION METHOD

CROSS-REFERENCE TO RELATED APPLICATION

This application claims priority to Japanese Application No. 2018-232502, filed Dec. 12, 2018, the disclosure of which is incorporated in its entirety by reference herein.

TECHNICAL FIELD

The present invention relates to an exhaust gas analysis apparatus for measuring component concentration in exhaust gas, an exhaust gas analysis method, and a correction expression creation method for the exhaust gas analysis apparatus.

BACKGROUND ART

In the past, a vehicle-mounted exhaust gas analysis apparatus mounted in a vehicle to measure component concentration in exhaust gas discharged from the vehicle has been provided with a hydrogen flame ionization detector (FID detector) that measures, for example, the concentration of total hydrocarbons (THC) or methane ($CH_4$) by mixing the exhaust gas and fuel gas for combustion and detecting the resulting ion current.

For example, in Patent Literature 1, a vehicle-mounted exhaust gas analysis apparatus having an FID detector is provided with a mechanism for discharging sample gas so as to keep a differential pressure in a sample gas flow path constant and a mechanism for taking in the atmosphere in order to suppress a variation in sample gas flow rate due to a variation in the atmospheric pressure around a vehicle.

CITATION LIST

Patent Literatures

Patent Literature 1: Japanese Unexamined Patent Application Publication No. 2018-96962

SUMMARY OF INVENTION

Technical Problem

However, even when the above-described mechanisms are provided, an error occurs in a measured value (THC concentration or $CH_4$ concentration) by the FID detector because of the variation in the surrounding atmospheric pressure. As a result of intensive examination by the present inventor, the cause of this may be that the supply amount of fuel gas supplied to the FID detector is varied by the variation in the surrounding atmospheric pressure and the hydrogen flame of the FID detector is changed.

Therefore, the present invention has been made in order to solve the above-described problem, and the main object thereof is to accurately measure exhaust gas component regardless of a variation in the atmospheric pressure around a test object that is a vehicle or part of it.

Solution to Problem

That is, the exhaust gas analysis apparatus according to the present invention is an exhaust gas analysis apparatus that measures component concentration in exhaust gas discharged from a test object that is a vehicle or part of it, and includes: an exhaust gas detector that mixes the exhaust gas and reactive gas together and detects the resulting phenomenon; a pressure gauge that measures the atmospheric pressure at the time of measurement of the exhaust gas or pressure at a predetermined point inside the exhaust gas analysis apparatus as measured pressure; and a correction part that, on the basis of the measured pressure by the pressure gauge, corrects the measurement error of the exhaust gas detector associated with a variation in the supply amount of the reactive gas.

In such a configuration, when the supply amount of the reactive gas is varied by a variation in the atmospheric pressure at the time of the measurement of the exhaust gas or in the pressure at the predetermined point inside the exhaust gas analysis apparatus, and a phenomenon occurring in the exhaust gas detector is changed, the measurement error of the exhaust gas detector associated with the variation in the supply amount of the reactive gas is corrected on the basis of the measured pressure by the pressure gauge, and therefore an exhaust gas component can be accurately measured.

Specifically, it is desirable that the correction part corrects the measurement error of the exhaust gas detector on the basis of the differential pressure between a reference pressure that is a measured pressure by the pressure gauge at the time of calibration curve creation and a measured pressure by the pressure gauge at the time of the measurement of the exhaust gas.

Specifically, it is desirable that the correction part corrects the measurement error of the exhaust gas detector by a correction expression (1) below:

[Expression 1]

$$C_C = \frac{C_1}{(1+ax)} \text{ where } x = \frac{Y-X}{X}. \quad (1)$$

Here, X represents the reference pressure, Y represents the measured pressure by the pressure gauge, a represents a constant, $C_1$ represents the measured component concentration, and $C_c$ represents the corrected measured component concentration.

This configuration makes it possible to obtain measured concentration at the reference pressure regardless of the atmospheric pressure at the time of the measurement of the exhaust gas or the pressure at the predetermined point inside the exhaust gas analysis apparatus.

In order to improve correction accuracy by the correction expression (1), it is desirable that the correction expression (1) is a second or higher order polynomial in x.

The measurement error of the exhaust gas detector occurs due to not only the supply amount of the reactive gas but also the concentration of the reactive gas. For this reason, it is desirable that the correction part corrects the measurement error of the exhaust gas detector on the basis of the difference between reactive gas concentration at the time of creation of the correction expression (1) and the concentration of the reactive gas supplied to the exhaust gas detector.

Specifically, it is desirable that the correction part corrects the measurement error of the exhaust gas detector by a correction expression (2) below:

[Expression 2]

$$C_C = \frac{C_1}{(1+aKx)} \text{ where } K = 1 - \left\{\alpha\frac{(B-A)}{A}\right\}. \quad (2)$$

Here, A represents the concentration of the reactive gas at the time of the creation of the correction expression (1), and B represents the concentration of the reactive gas supplied at the time of the measurement of the exhaust gas. Also, α represents a constant.

This configuration makes it possible to correct the measurement error due to a variation in the concentration of the reactive gas supplied at the time of the measurement only by adding the coefficient K to the correction expression (1).

Specifically, it is conceivable that the exhaust gas detector is an FID detector, and the reactive gas is hydrogen.

As a configuration for supplying the fuel gas to the FID detector, it is conceivable to connect a fuel gas cylinder in which the fuel gas is enclosed. The fuel gas cylinder has to be replaced when the fuel gas inside is used up. There is a variation among the hydrogen concentrations of fuel gas enclosed in respective fuel gas cylinders. This variation causes the measurement error of the FID detector. In order to solve this problem, it is desirable that the correction part updates the correction expression (2) every time the hydrogen gas cylinder is replaced.

Also, it is desirable that the exhaust gas analysis apparatus includes: the hydrogen gas cylinder in which the hydrogen gas is enclosed; an inert gas cylinder in which inert gas is enclosed; and a mixing mechanism that mixes the hydrogen gas from the hydrogen gas cylinder and the inert gas from the inert gas cylinder together at a predetermined ratio, and mixed gas resulting from mixing by the mixing mechanism is supplied to the FID detector as the fuel gas. In this case, it is desirable that the hydrogen gas cylinder is one enclosing the hydrogen gas having a concentration of 100% and the inert gas cylinder is one enclosing the inert gas having a concentration of 100%.

In this configuration, the mixing mechanism performs the mixing so that the hydrogen gas has a predetermined concentration, and therefore it is not necessary to take account of a variation in the hydrogen concentration of the fuel gas occurring when a fuel gas cylinder is used.

The effect of the present invention becomes further noticeable when the above-described exhaust gas analysis apparatus is a vehicle-mounted one mounted in a test object, which is a vehicle or part of it, to measure a component of exhaust gas discharged from the test object. This is because, in the case of the vehicle-mounted one, a variation in surrounding pressure is likely to occur along with running of it.

Also, the exhaust gas analysis method according to the present invention is an exhaust gas analysis method using an exhaust gas analysis apparatus having an exhaust gas detector that mixes exhaust gas discharged from a vehicle and reactive gas together and detects the resulting phenomenon, and the exhaust gas analysis method measures the atmospheric pressure at the time of measurement of the exhaust gas or pressure at a predetermined point inside the exhaust gas analysis apparatus as measured pressure; and on the basis of the measured pressure, corrects the measurement error of the exhaust gas detector associated with a variation in the supply amount of the reactive gas.

This exhaust gas analysis method corrects the measurement error of the exhaust gas detector associated with the variation in the supply amount of the reactive gas on the basis of the measured pressure by the pressure gauge, and can therefore accurately measure an exhaust gas component regardless of a variation in the atmospheric pressure around a test object that is a vehicle or part of it.

Further, the correction expression (1) creation method for the exhaust gas analysis apparatus according to the present invention connects a pressure changing device to an exhaust gas introduction port and an exhaust gas discharge port of the exhaust gas analysis apparatus, depressurizes or pressurizes the exhaust gas introduction port and the exhaust gas discharge port by the pressure changing device, in the resulting depressurized or pressurized state, introduces calibration gas from a calibration gas introduction port of the exhaust gas analysis device, and creates the correction expression (1) with use of a measured value by the exhaust gas analysis apparatus and a known concentration of the calibration gas at a reference atmospheric pressure.

This correction expression creation method can reproduce the depressurized or pressurized state for the vehicle-mounted exhaust gas analysis apparatus without using a pressurizing/depressurizing test chamber. Accordingly, the correction expression (1) can be created by an inexpensive and simplified method. Also, the correction expression (1) can be easily updated for each of vehicle-mounted exhaust gas analysis apparatuses after shipment at a corresponding shipping destination or the like.

Advantageous Effects of Invention

According to the present invention described above, an exhaust gas component can be accurately measured regardless of a variation in the atmospheric pressure around a test object that is a vehicle or part of it.

DESCRIPTION OF EMBODIMENTS

Figure 1:
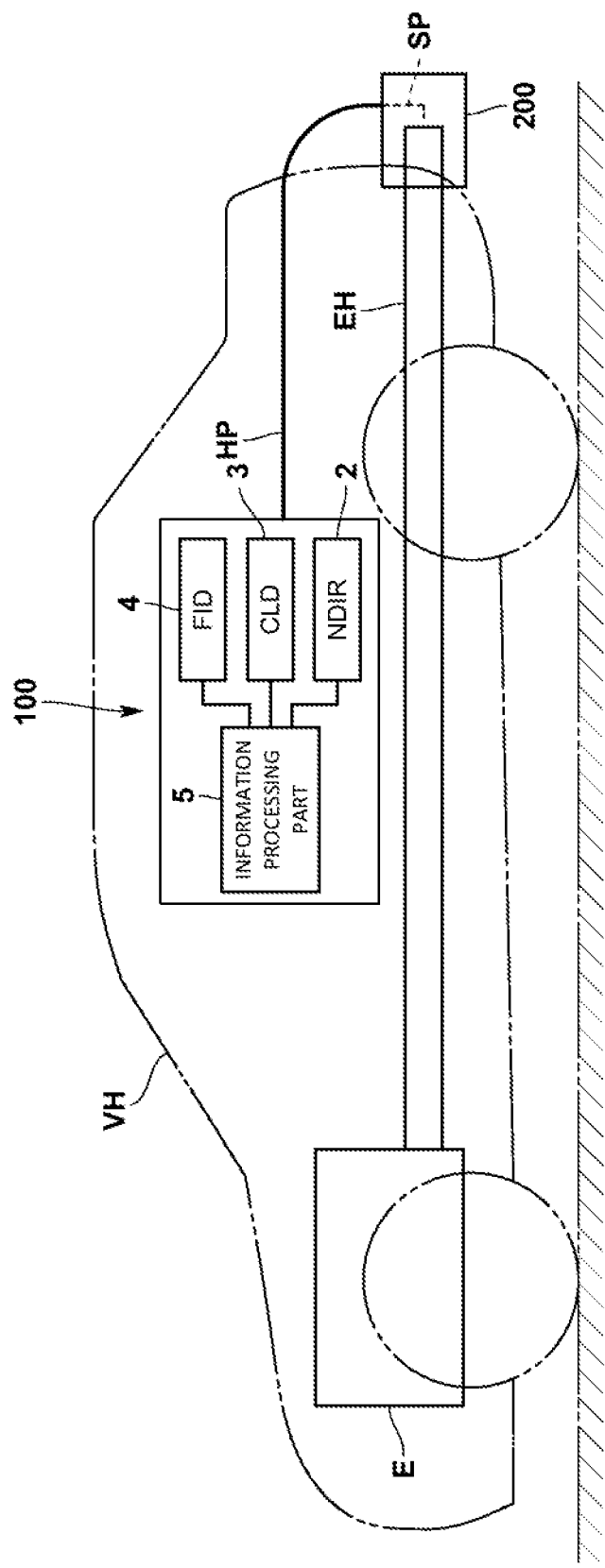
FIG. 1 is an overall schematic diagram of a vehicle-mounted exhaust gas analysis apparatus according to one embodiment of the present invention.

In the following, a vehicle-mounted exhaust gas analysis apparatus 100 according to one embodiment of the present invention will be described with reference to the drawings.

The vehicle-mounted exhaust gas analysis apparatus 100 of the present embodiment is one mounted in a vehicle VH such as a car to measure component concentration in exhaust gas discharged from the vehicle VH. In addition, the vehicle-mounted exhaust gas analysis apparatus 100 can be used for a real driving emission (RDE) test.

The vehicle-mounted exhaust gas analysis apparatus 100 is one that measures the component concentration in the exhaust gas sampled by an exhaust gas sampling mechanism 200 such as a sampling pipe SP for sampling the whole or part of the exhaust gas discharged through an exhaust pipe EH connected to the engine E of the vehicle VH. In addition, the exhaust gas sampled by the exhaust gas sampling mechanism 200 is heated to or kept at a predetermined temperature by a heating pipe HP, and then introduced to the vehicle-mounted exhaust gas analysis apparatus 100.

Specifically, the vehicle-mounted exhaust gas analysis apparatus 100 is one that analyzes a measurement target component such as carbon monoxide (CO), carbon dioxide ($CO_2$), nitrogen oxides ($NO_X$), methane ($CH_4$), or total hydrocarbons (THC), and in the present embodiment, includes an NDIR detector 2 using a non-dispersive infrared absorption (NDIR) method, a CLD detector 3 using a chemiluminescence (CLD) method, and an FID detector 4 using a hydrogen flame ionization (FID) method. In addition, the present embodiment has the NDIR detector 2, CLD detector 3, and FID detector 4, but may be one having only the FID detector 4 as an exhaust gas detector.

The NDIR detector 2 is one that continuously measures the concentration of carbon monoxide (CO) or carbon dioxide ($CO_2$) contained in the exhaust gas. The CLD detector 3 is one that continuously measures the concentration of $NO_X$ or nitrogen monoxide (NO) contained in the exhaust gas. The FID detector 4 is one that continuously measures the concentration of methane ($CH_4$) or total hydrocarbons (THC) contained in the exhaust gas. In addition, the vehicle-mounted exhaust gas analysis apparatus 100 can be provided with various analyzers correspondingly to measurement target components. The various analyzers are such as a PMD meter using a magnetic pressure (PMD) method, an FTIR meter using a Fourier transform infrared spectroscopic (FTIR) method, and a QCL-IR meter using a mid-infrared laser spectroscopic (QCL-IR) method.

Further, analysis data obtained by these analyzers 2 to 4 is outputted to an information processing part 5, and the information processing part 5 processes, records, or displays the analysis data. In addition, the above-described multiple analyzers may be respectively provided as separate bodies.

Figure 2:
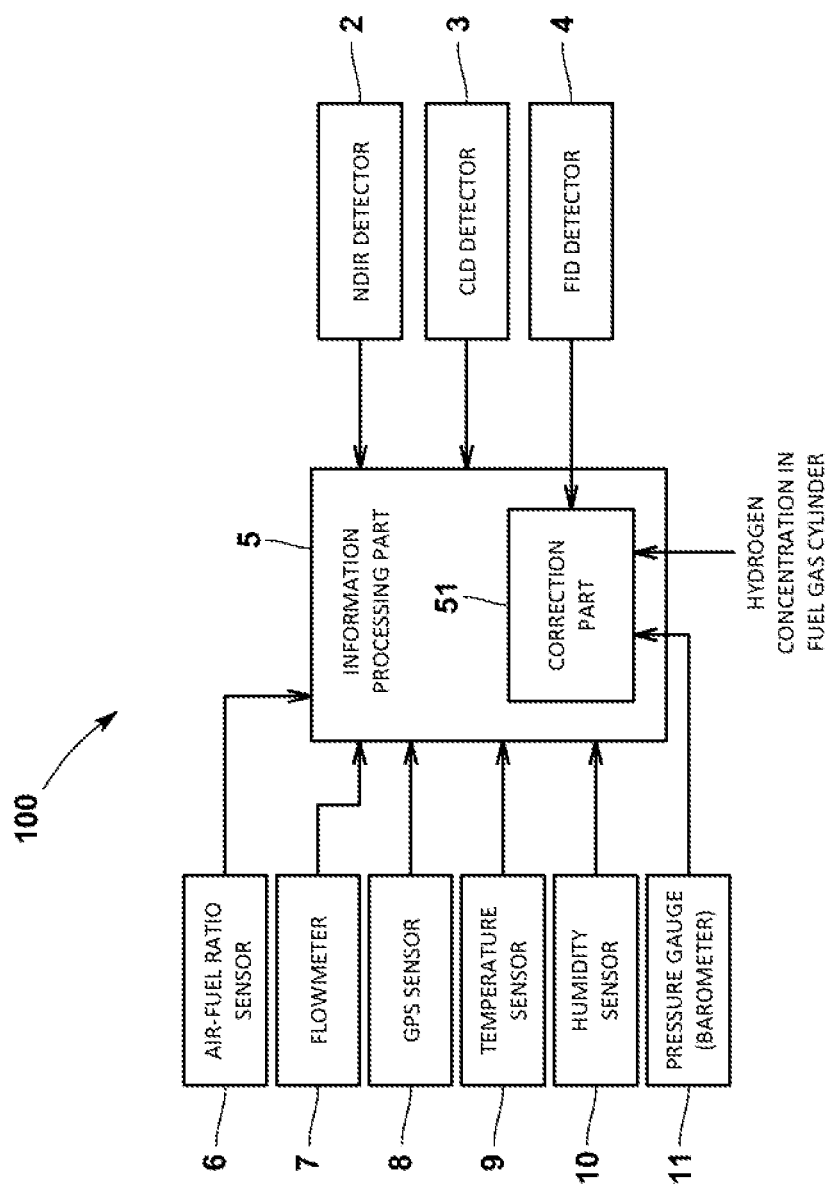
FIG. 2 is a functional block diagram of an information processing part in the same embodiment.

The information processing part 5 is a dedicated or general-purpose computer including a CPU, an internal memory, an AD converter, an input/output inverter, and the like, and acquires not only the analysis data by the analyzers 2 to 4 but data acquired from another sensor group to process, record, or display it. In addition, as illustrated in FIG. 2, the sensor group has at least a pressure gauge (barometer) 11 that measures the pressure outside the vehicle (atmospheric pressure). Besides, the sensor group may be one having: an air-fuel ratio sensor 6 that measures the air fuel ratio (A/F) of the vehicle; a flowmeter 7 that measures the flow rate of the exhaust gas discharged through the exhaust pipe; a GPS sensor 8 that detects the position of the vehicle; a temperature sensor 9 that measures the temperature outside the vehicle; a humidity sensor 10 that measures the humidity outside the vehicle, and the like.

Figure 3:
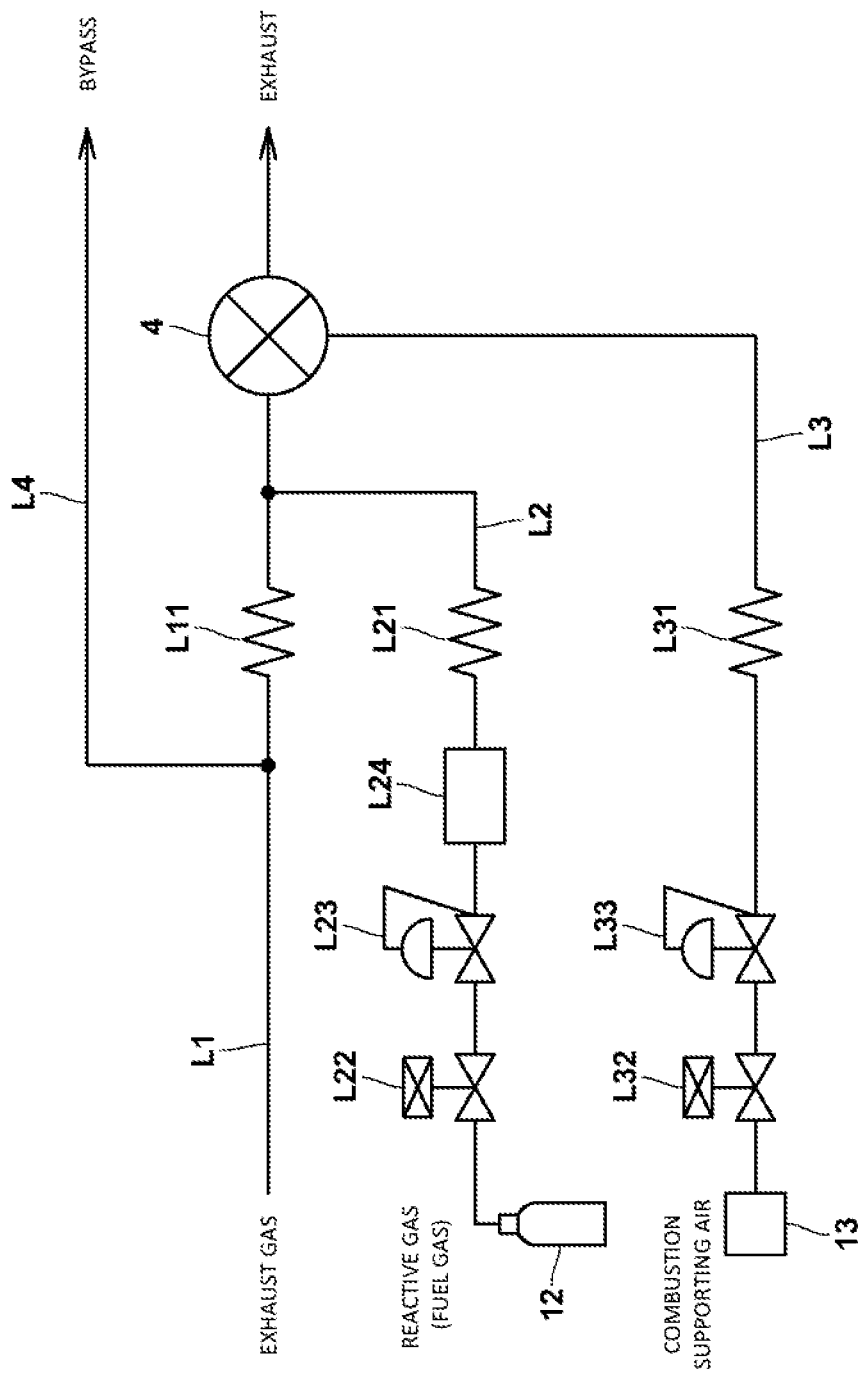
FIG. 3 is a schematic diagram illustrating an example of gas flow for an FID detector in the same embodiment.

As illustrated in FIG. 3, the FID detector 4 of the vehicle-mounted exhaust gas analysis apparatus 100 is connected with: an exhaust gas introduction line L1 for introducing the exhaust gas; a fuel gas line L2 for introducing reactive gas (fuel gas) serving as fuel for hydrogen flame produced in the FID detector 4; and a combustion supporting air line L3 for introducing combustion supporting air for supporting the combustion of the fuel gas.

The exhaust gas introduction line L1 is provided with a flow rate control device L11 such as a capillary or an orifice, and the upstream side of the flow rate control device 11 may be connected with a bypass line L4 for exhausting part of the exhaust gas. The exhaust gas introduction line L1 is introduced with part of the exhaust gas sampled by the exhaust gas sampling mechanism 200.

The fuel gas line L2 is provided with a flow rate control device L21 such as a capillary or an orifice. The fuel gas line L2 is connected with a fuel gas cylinder 12 in which the fuel gas is enclosed, and from the fuel gas cylinder 12, the fuel gas is supplied. The fuel gas in the fuel gas cylinder 12 in the present embodiment is mixed gas in which helium and hydrogen are mixed and hydrogen concentration is controlled to 40%±2%. In addition, the fuel gas line L2 may be provided with an on-off valve L22, a pressure regulation valve L23, a filter L24, and the like as necessary.

The combustion supporting air line L3 is provided with a flow rate control device L31 such as a capillary or an orifice. The combustion supporting air line L3 is connected with a gas cleaning device 13 as necessary, and air cleaned by the gas cleaning device 13 is supplied. In addition, the combustion supporting air line L3 may be provided with an on-off valve L32, a pressure regulation valve L33, and the like as necessary.

The exhaust gas introduction line L1 and the fuel gas line L2 are merged together before being connected to the FID detector 4, and the exhaust gas is introduced into the hydrogen flame through a nozzle together with the fuel gas. When HC is contained in the exhaust gas, part of it is ionized in the hydrogen flame. In addition, there is a potential difference between a collector electrode around the nozzle and the nozzle, and therefore between them, an ion current corresponding to an ion production amount flows. The value of the current is substantially proportional to the amount of carbon contained in the HC in the exhaust gas, and therefore by detecting the current value, THC concentration is measured.

Further, as illustrated in FIG. 2, the information processing part 5 in the present embodiment includes a correction part 51 that, on the basis of the measured pressure by the pressure gauge 11, corrects the measurement error of the FID detector 4 associated with a variation in the supply amount of the fuel gas. In addition, the measurement error of the FID detector 4 associated with the variation in the supply amount of the fuel gas occurs because the supply amount of the fuel gas supplied to the FID detector 4 through the fuel gas line L2 is varied by a variation in the atmospheric pressure. Further, the variation in the supply amount of the fuel gas occurs because the differential pressure between the upstream side pressure and downstream side pressure of the flow rate control device L21 provided in the fuel gas line L2 is changed.

Specifically, the correction part 51 corrects the measurement error of the FID detector 4 on the basis of the differential pressure between a reference pressure at the time of calibration curve creation and a measured pressure by the pressure gauge 11 at the time of exhaust gas measurement. In addition, the reference pressure may be measured pressure by the pressure gauge 11 at the time of the calibration curve creation, or measured pressure by another pressure gauge at the time of the calibration curve creation.

In more detail, the correction part 51 corrects the measurement error of the FID detector 4 by the correction expression (1) below.

[Expression 3]

$$C_C = \frac{C_1}{(1+ax)} \text{ where } x = \frac{Y-X}{X}. \qquad (1)$$

Here, X represents the reference pressure, and Y represents the measured pressure by the pressure gauge 11.

The correction expression (1) is created using a pressure regulation system that regulates the surrounding pressure or internal pressure of the vehicle-mounted exhaust gas analysis apparatus 100. The correction expression (1) is created by introducing calibration gas to the vehicle-mounted exhaust gas analysis apparatus 100 under respective pressure conditions in the pressure regulation system and using measured values by the FID detector 4 under the respective pressure conditions and the known concentration of the calibration gas at a reference atmospheric pressure.

Specifically, as the pressure regulation system, it is conceivable to use a pressure regulation chamber capable of containing the vehicle-mounted exhaust gas analysis apparatus 100 and also regulating internal pressure or a simplified pressure regulator capable of being connected to the vehicle-mounted exhaust gas analysis apparatus 100 to regulate the internal pressure of the vehicle-mounted exhaust gas analysis apparatus 100.

The pressure regulation chamber includes: a chamber in which the vehicle-mounted exhaust gas analysis apparatus 100 is contained: a pump that depressurizes or pressurizes the inside of the chamber; and a pressure sensor that detects the pressure inside the chamber. In addition, the pump is controlled so that the detected pressure by the pressure sensor reaches a predetermined pressure, and thereby the surrounding pressure of the vehicle-mounted exhaust gas analysis apparatus 100 is regulated. The correction expression (1) is created by introducing the calibration gas to the vehicle-mounted exhaust gas analysis apparatus 100 under the respective pressure conditions and using the measured values by the FID detector 4 under the respective pressure conditions and the known concentration of the calibration gas at the reference atmospheric pressure. In addition, when the pressure regulation chamber is used every time the fuel gas cylinder is changed, it costs time and money to create the pressure correction expression.

The simplified pressure regulator includes: a connection line connected to an exhaust gas introduction port and an exhaust gas discharge port of the vehicle-mounted exhaust gas analysis apparatus 100; a pump that is provided in the connection line and depressurizes or pressurizes an internal flow path of the vehicle-mounted exhaust gas analysis apparatus 100 via the exhaust gas introduction port and the exhaust gas discharge port; and a pressure sensor that detects the pressure of the internal flow path of the vehicle-mounted exhaust gas analysis apparatus 100. Also, as the pressure sensor, one provided for the vehicle-mounted exhaust gas analysis apparatus 100 may be used. In addition, the pump is controlled so that the detected pressure by the pressure sensor reaches a predetermined pressure, and thereby the internal pressure of the vehicle-mounted exhaust gas analysis apparatus 100 is regulated. The correction expression (1) is created by introducing the calibration gas from a calibration gas introduction port of the vehicle-mounted exhaust gas analysis apparatus 100 under the respective pressure conditions, and using the measured values by the FID detector 4 under the respective pressure conditions and the known concentration of the calibration gas at the reference atmospheric pressure.

In this case, the vehicle-mounted exhaust gas analysis apparatus 100 may be in a state of being mounted in the vehicle or in a state of being dismounted from the vehicle.

Further, a measured value by the FID detector 4 is varied also depending on hydrogen concentration in the fuel gas enclosed in the fuel gas cylinder 12 connected to the fuel gas line L2. For this reason, the correction part 51 can also correct the measurement error of the FID detector 4 on the basis of the hydrogen concentration in the fuel gas.

Specifically, the correction part 51 corrects the measurement error of the FID detector 4 on the basis of the difference between hydrogen concentration in the fuel gas at the time of correction expression (1) creation and hydrogen concentration in the fuel gas supplied to the FID detector 4.

In more detail, the correction part 51 corrects the measurement error of the FID detector 4 by the correction expression (2) below.

[Expression 4]

$$C_C = \frac{C_1}{(1 + aKx)} \text{ where } K = 1 - \left\{\alpha \frac{(B - A)}{A}\right\}. \quad (2)$$

Here, A represents the hydrogen concentration in the fuel gas at the time of the correction expression (1) creation, and B represents the hydrogen concentration in the fuel gas (in a replaced fuel gas cylinder) supplied at the time of the measurement. Also, $\alpha$ represents a constant.

Note that the correction part 51 updates the correction expression (2) every time the fuel gas cylinder 12 is replaced. In detail, the correction part 51 updates the correction expression (2) by acquiring the hydrogen concentration B in the replaced fuel gas cylinder 12 and calculating the coefficient K using the hydrogen concentration B. In addition, the hydrogen concentration B in the replaced fuel gas cylinder 12 may be inputted by a user, or data on the hydrogen concentration B may be configured to be automatically transmitted to the information processing part 5 by connecting the fuel gas cylinder 12.

The correction part 51 may be adapted to update the correction expression (2) using software preliminarily stored in the memory of the information processing part 5. For example, the correction expression (2) is updated in such a manner that, using the software, the information processing part 5 senses that the fuel gas cylinder 12 has been replaced, and acquires the data on the hydrogen concentration in the replaced fuel gas cylinder 12 to calculate the coefficient K.

In the vehicle-mounted exhaust gas analysis apparatus 100 of the present embodiment configured as described, since the supply amount of the fuel gas is varied by the variation in the atmospheric pressure around the vehicle, and even when the hydrogen flame of the FID detector 4 is changed, the measurement error of the FID detector 4 associated with the variation in the supply amount of the fuel gas is corrected on the basis of the measured atmospheric pressure by the pressure gauge 11, an exhaust gas component can be accurately measured regardless of the variation in the surrounding atmospheric pressure associated with the movement of the vehicle.

Note that the present invention is not limited to the above-described embodiment.

For example, the correction expression (1) in the above-described embodiment is a linear function, but may be a quadratic or higher order function. Similarly, the correction expression (2) may also be a quadratic or higher order function.

Figure 4:
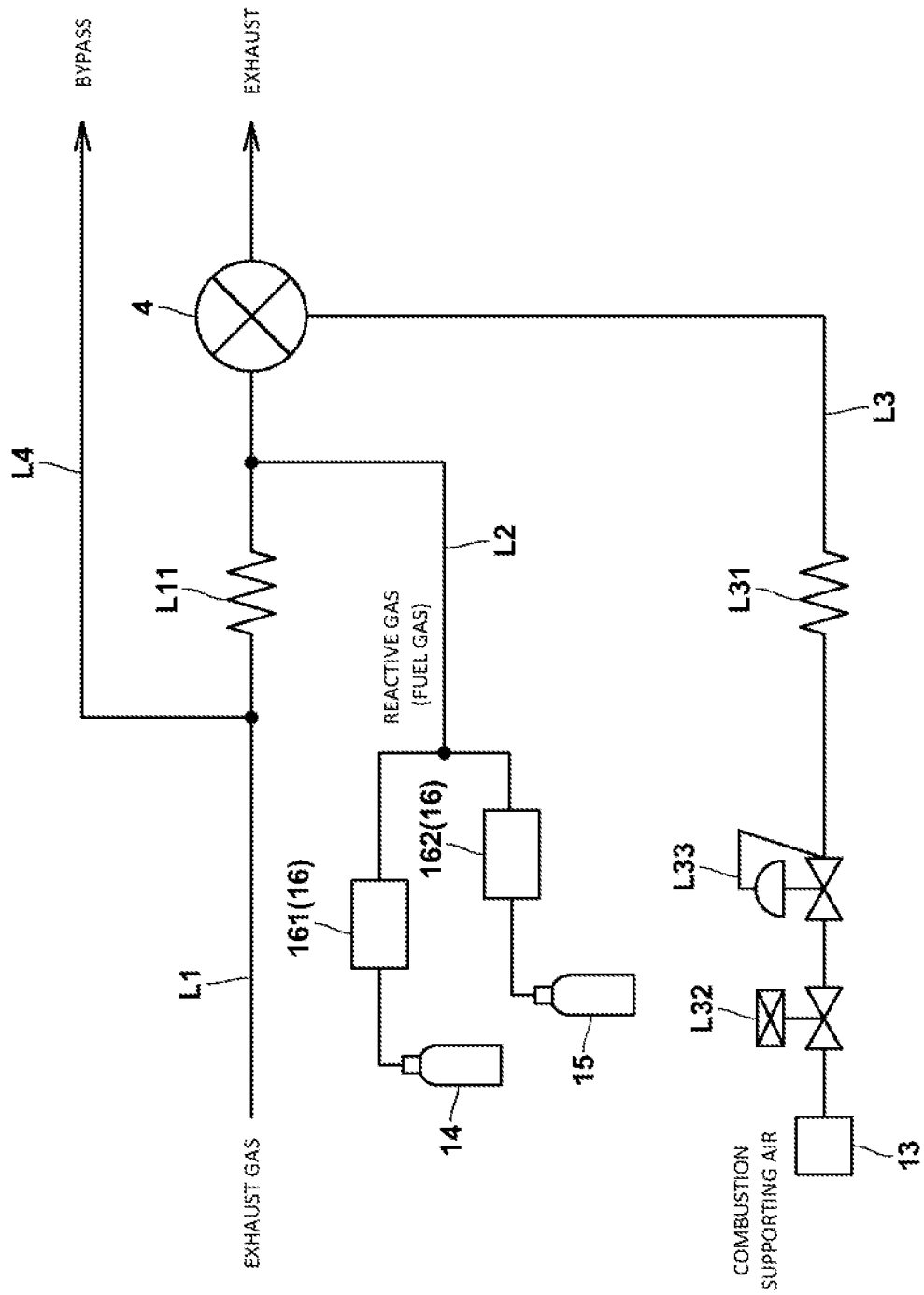
FIG. 4 is a schematic diagram illustrating an example of gas flow for the FID detector in a variation.

In addition, the above-described embodiment is configured to introduce the fuel gas from the fuel gas cylinder 12 to the fuel gas line L2, but as illustrated in FIG. 4, may be adapted to include: a hydrogen gas cylinder 14 in which hydrogen gas is enclosed; an inert gas cylinder 15 in which inert gas is enclosed; and a mixing mechanism 16 that mixes the hydrogen gas from the hydrogen gas cylinder 14 and the inert gas from the inert gas cylinder 15 at a predetermined ratio, and to supply mixed gas resulting from mixing by the mixing mechanism 16 to the FID detector 4 as the fuel gas.

The hydrogen gas cylinder 14 is one for supplying the hydrogen gas having a concentration of 100%, and the inert gas cylinder is one for supplying the inert gas having a concentration of 100%. Also, the mixing mechanism 16 is configured using a first flow rate regulation part 161 that regulates the flow rate of the hydrogen gas, such as a mass flow controller (MFC), and a second flow rate regulation part 162 that regulates the flow rate of the inert gas, such as a mass flow controller (MFC). The mixed gas whose ratio (e.g., hydrogen gas:inert gas=4:6) is regulated by the flow rate regulation parts 161 and 162 is supplied to the fuel gas line L2.

The flow rate control device provided in each of the lines in the above-described embodiment is a constant flow rate device such as a capillary or an orifice, but may be one using a flow rate regulation valve, such as a mass flow controller.

The pressure gauge 11 in the above-described embodiment is one that measures the atmospheric pressure around the test object that is the vehicle or part of it, but may be one that measures pressure at a predetermined point of the exhaust gas analysis apparatus, such as the inside of the flow path between the reactive gas cylinder (fuel gas cylinder 12) and the exhaust gas detector (FID detector 4).

In the above-described embodiment, the correction part 51 is one that corrects the measurement error of the FID detector 4, but may be one that corrects the measurement error of another exhaust gas detector such as the CLD detector 3. In the case of the CLD detector 3, the measurement error of the CLD detector 3 associated with a variation in the supply amount of ozone gas as reactive gas supplied to the CLD detector 3 is corrected. In the exhaust gas analysis apparatus 100, the CLD detector 3 detects a phenomenon (the amount of luminescence) occurring when NO contained in the exhaust gas and ozone react, and the correction part 51 corrects the measurement error of a measured value based on the amount of luminescence.

The information processing part 5 of the exhaust gas analysis apparatus may be one that calculates the discharge amount of each component using measured concentrations obtained by the respective detectors 2 to 4 and the exhaust gas flow rate obtained by the flowmeter 7.

Figure 5:
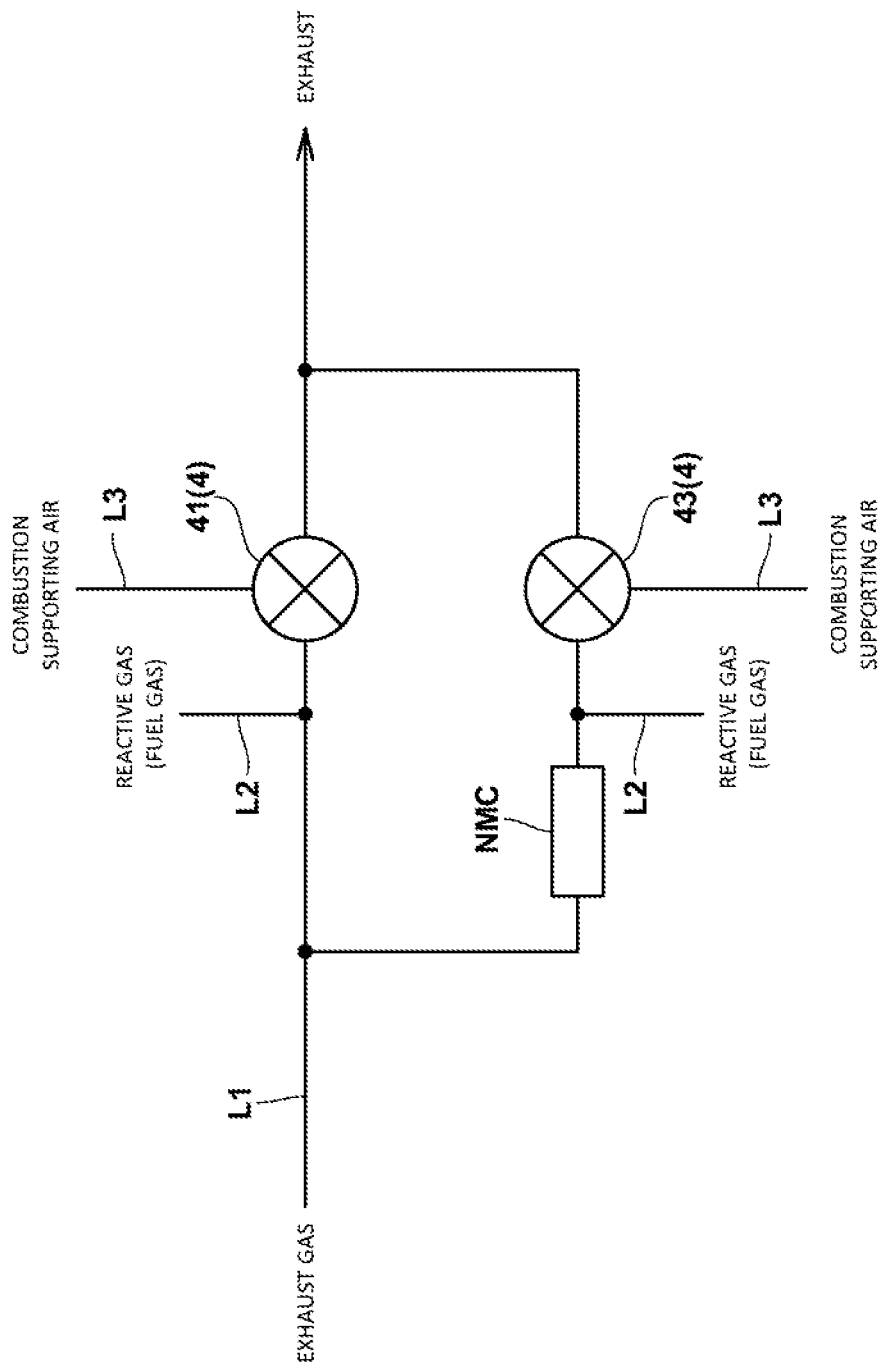
FIG. 5 is a schematic diagram illustrating an example of gas flow for FID detectors in a variation.

As illustrated in FIG. 5, the exhaust gas analysis apparatus 100 may be one having two FID detectors 41 and 42. In this configuration, the exhaust gas line L1 is branched to provide the resulting branches in parallel, and the branched flow path to the FID detector 42 is provided with a non-methane cutter (NMC). In addition, this exhaust gas analysis apparatus is configured to detect THC in the exhaust gas by the FID detector 41 and detect $CH_4$ in the exhaust gas by the FID 42. This configuration makes it possible for the information processing part 5 to, on the basis of measured values by the FID 41 and FID 42, calculate total hydrocarbon concentration and methane concentration, and also on the basis of the difference between them, calculate non-methane hydrocarbon concentration (NMHC) included in the exhaust gas.

The above-described embodiment is a vehicle-mounted one but may be a stationary one.

Besides, various modifications and combinations of the embodiments may be made without departing from the scope of the present invention.

REFERENCE SIGNS LIST

100: Vehicle-mounted exhaust gas analysis apparatus
4: FID detector (exhaust gas detector)
11: Pressure gauge
51: Correction part

The invention claimed is:

1. An exhaust gas analysis apparatus that measures component concentration in exhaust gas discharged from a test object that is a vehicle or part of it, the exhaust gas analysis apparatus comprising:
an exhaust gas detector that mixes the exhaust gas and reactive gas together and detects a resulting phenomenon;
a pressure gauge that measures atmospheric pressure at a time of measurement of the exhaust gas or pressure at a predetermined point inside the exhaust gas analysis apparatus as measured pressure; and
a correction part that, on a basis of the measured pressure by the pressure gauge, corrects a measurement error of the exhaust gas detector, the measurement error being associated with a variation in a supply amount of the reactive gas.

2. The exhaust gas analysis apparatus according to claim 1, wherein
the correction part corrects the measurement error of the exhaust gas detector on a basis of a differential pressure between a reference pressure that is a measured pressure by the pressure gauge at a time of calibration curve creation and a measured pressure by the pressure gauge at a time of the measurement of the exhaust gas.

3. The exhaust gas analysis apparatus according to claim 1, wherein
the correction part corrects the measurement error of the exhaust gas detector by a correction expression (1) below:

$$C_C = \frac{C_1}{(1+ax)} \text{ where } x = \frac{Y-X}{X} \text{ and} \quad (1)$$

here, X represents a reference pressure, Y represents the measured pressure by the pressure gauge, a represents a constant, $C_1$ represents the measured component concentration, and $C_c$ represents corrected measured component concentration.

4. The exhaust gas analysis apparatus according to claim 3, wherein
the correction expression (1) is a second or higher order polynomial in x.

5. The exhaust gas analysis apparatus according to claim 3, wherein
the correction part corrects the measurement error of the exhaust gas detector on a basis of a difference between concentration of the reactive gas at a time of creation of the correction expression (1) and concentration of the reactive gas supplied to the exhaust gas detector.

6. The exhaust gas analysis apparatus according to claim 5, wherein
the correction part corrects the measurement error of the exhaust gas detector by a correction expression (2) below:

$$C_C = \frac{C_1}{(1+aKx)} \text{ where } K = 1 - \left\{\alpha\frac{(B-A)}{A}\right\} \text{ and} \quad (2)$$

here, A represents the concentration of the reactive gas at the time of the creation of the correction expression (1), B represents the concentration of the reactive gas supplied at the time of the measurement of the exhaust gas, and α represents a constant.

7. The exhaust gas analysis apparatus according to claim 6, wherein
the exhaust gas detector is a hydrogen flame ionization detector, and the reactive gas is hydrogen.

8. The exhaust gas analysis apparatus according to claim 7, wherein
the hydrogen flame ionization detector is connected with a hydrogen gas cylinder in which hydrogen is enclosed as the reactive gas, and
the correction part updates the correction expression (2) every time the hydrogen gas cylinder is replaced.

9. The exhaust gas analysis apparatus according to claim 8, comprising:
the hydrogen gas cylinder in which the hydrogen gas is enclosed;
an inert gas cylinder in which inert gas is enclosed; and
a mixing mechanism that mixes the hydrogen gas from the hydrogen gas cylinder and the inert gas from the inert gas cylinder together at a predetermined ratio, wherein
mixed gas resulting from mixing by the mixing mechanism is supplied to the hydrogen flame ionization detector as fuel gas.

10. The exhaust gas analysis apparatus according to claim 1, being a vehicle-mounted one mounted in a test object to measure a component of exhaust gas discharged from the test object, the test object being a vehicle or part of the vehicle.

11. An exhaust gas analysis method using an exhaust gas analysis apparatus having an exhaust gas detector that mixes exhaust gas discharged from a vehicle and reactive gas together and detects a resulting phenomenon, the exhaust gas analysis method comprising:
measuring atmospheric pressure at a time of measurement of the exhaust gas or pressure at a predetermined point inside the exhaust gas analysis apparatus as measured pressure; and
on a basis of the measured pressure, correcting a measurement error of the exhaust gas detector, the measurement error being associated with a variation in a supply amount of the reactive gas.

12. A correction expression creation method for creating the correction expression (1) in the exhaust gas analysis apparatus according to claim 3, the correction expression creation method comprising:
connecting a pressure changing device to an exhaust gas introduction port and an exhaust gas discharge port of the exhaust gas analysis apparatus;
depressurizing or pressurizing the exhaust gas introduction port and the exhaust gas discharge port by the pressure changing device, in a resulting depressurized or pressurized state;
introducing calibration gas from a calibration gas introduction port of the exhaust gas analysis device; and
creating the correction expression (1) with use of a measured value by the exhaust gas analysis apparatus and a known concentration of the calibration gas at a reference atmospheric pressure.

* * * * *